United States Patent [19]

LeGrand et al.

[11] Patent Number: 4,583,407
[45] Date of Patent: Apr. 22, 1986

[54] METHOD FOR ACCELERATING THE FAILURE OF COATINGS

[75] Inventors: Donald G. LeGrand, Burnt Hills; William V. Olszewski, Stillwater, both of N.Y.

[73] Assignee: General Electric Company, Schenectady, N.Y.

[21] Appl. No.: 612,529

[22] Filed: May 21, 1984

[51] Int. Cl.[4] .............................................. G01N 3/20
[52] U.S. Cl. ..................................... 73/762; 73/85 L
[58] Field of Search ............... 73/762, 849, 85 L, 856, 73/432 SD

[56] References Cited

U.S. PATENT DOCUMENTS 2,032,989  3/1936  Kenney et al. ..................... 73/85 L
3,541,846  11/1970  Stolki ..................... 73/762

Primary Examiner—Anthony V. Ciarlante
Attorney, Agent, or Firm—Richard J. Traverso; James C. Davis, Jr.; James Magee, Jr.

[57] ABSTRACT

A method of accelerating tests for the delayed failure of coatings and coated substrates caused by degradation is provided wherein the coated substrate is subjected to a controlled level of strain during testing.

7 Claims, 1 Drawing Figure

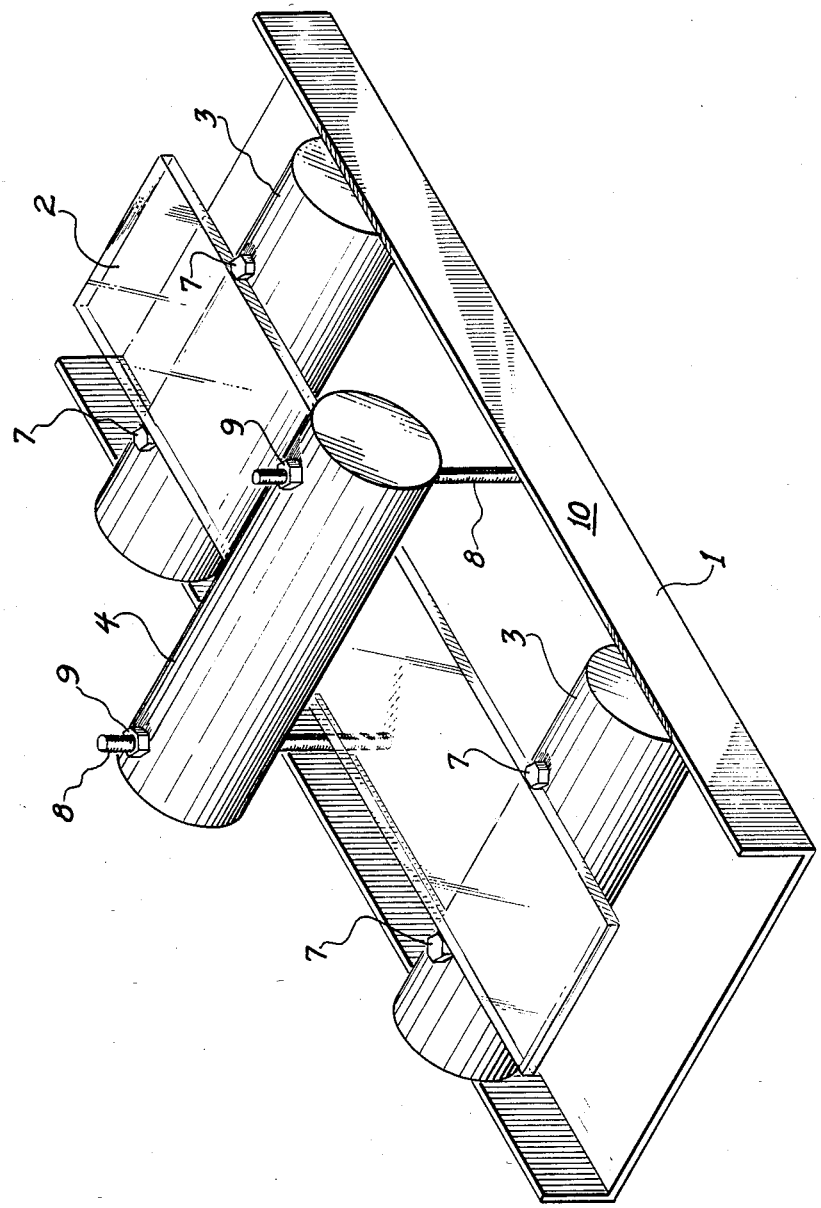

METHOD FOR ACCELERATING THE FAILURE OF COATINGS

BACKGROUND OF THE INVENTION

This invention is related to the art of testing the weatherability and expected lifetime of coatings and coated substrates. More particularly, this invention relates to a method for accelerating the delayed failure of coatings, thus shortening the time necessary to test the samples.

Methods of accelerating the delayed failure of coatings are very important for the evaluation of new coatings as well as the modification or improvement of old coatings. The phrase "delayed failure" as used herein refers to the degradation of coatings, i.e. delamination, yellowing, cracking, etc.; which results after a period of time from prolonged exposure to the elements. These "elements" include, but are not limited to, moisture, humidity, heat and ultraviolet light. Previous methods for accelerating the delayed failure of paints, silicone resin coatings, laminates and other coatings have included Florida tests, QUV tests and stress resistance tests. All tests serve to expose the coatings to severe environments so as to accelerate the degradation which occurs under normal use. These tests permit rapid comparisons of new or modified coatings to existing coatings.

The phrase "Florida tests", as used herein, describes an accelerated test which involves placing a coated sample in a field testing site in Florida, where the heat, humidity and ultraviolet light exposure is unusually high. Coatings will fail under these conditions much earlier than in environments where the coatings will be used. The phrase, "QUV tests", as used herein, describes accelerated laboratory tests wherein a coated sample is alternately exposed to high levels of ultraviolet light at high temperatures and high levels of humidity in darkness. The conditions under Florida tests are relatively moderate, with coated substrates often taking months and years to show any signs of failure. The conditions under QUV tests are more severe and some samples, such as silicone resin coated samples, undergo failure after a number of hours or days. However, with the constant improvement of coatings, the time of failure is getting longer and longer.

Anthony and LeGrand disclose a method of evaluating the stress resistance of coated substrates in copending application, Ser. No. 572,482. These tests are instantaneous in that measurements relating to stress resistance at the time of failure can be obtained without waiting for degradation of the coating. Although this method of analysis does provide useful information concerning the coated substrates and does suggest the relative performance of coated substrates when exposed to the elements described above, the utility of these tests is somewhat limited. The actual degradation of the coating is not tested during stress analysis since the coating is not permitted to degrade. Degradation of a coating is a complicated phenomenon which is effected by factors other than the physical forces reflected by stress analysis. In particular, the effects which ultraviolet light and humidity have on the coated substrate are not reflected by stress analysis.

This invention provides a method for accelerating the delayed failure of coatings and coated substrates caused by exposure to various elements, some of which have been described above. This process permits a rapid evaluation of the degradation of coatings and coated substrates. The time necessary for testing the coatings can be reduced by 1-2 orders of magnitude.

SUMMARY OF THE INVENTION

A method for accelerating tests for the delayed failure time of coatings and coated substrates is provided, said method comprising subjecting said coated substrate to a controlled level of strain and testing the delayed failure time of the coated substrate. Typical tests utilized to determine the delayed failure time are Florida tests and QUV tests. Coated substrates which have performed well under these accelerated conditions are silicon resin coated articles, in particular, polycarbonate resin substrates.

OBJECTS OF THE INVENTION

An object of the present invention is to shorten the time necessary to achieve delayed failure of coated substrates.

Another object of the present invention is to provide a method which requires less time to evaluate a coating's resistance to degradation which utilizes conventional delayed failure tests.

DESCRIPTION OF THE DRAWING

The drawing is a perspective view of an apparatus which is capable of providing various levels of strain to a coated substrate and is suitable for performing steps in the process comprising this invention.

DETAILED DESCRIPTION OF THE PREFERRED EMBODIMENTS

The desired objects of this invention and other objects are achieved by applying a controlled level of strain to a coated substrate to be tested for delayed failure. The process comprising this invention is useful in severe field environments, such as the Florida tests, and in accelerated laboratory tests, such as QUV tests. The process essentially involves accelerating the degradation of coated samples being tested by subjecting the coated substrate to a certain level of strain.

Where the level of strain is predetermined or controlled, the failure times obtained by various tests provide good comparative data against that obtained from other coated substrates which were tested under the same degree or level of strain. The force or stress applied to the coated substrate may have any direction. The force can be extensional, torsional, etc., so long as the specimen is deformed. To obtain reliable comparative data from a number of samples of coated substrates, the forces applied to each sample must also have the same direction besides being of the same magnitude. Different forces may have a different effect on degradation and may accelerate the delayed failure at a different rate.

The lifetime of a coated sample will degrade proportionately with the amount of stress applied to that sample during testing. Although not a linear relationship, the failure times for a coated sample can be predicted at various levels of strain, including zero strain, by extrapolations made with previously obtained data.

Any apparatus which applies a constant level of strain to a coated substrate and which can reproduce this level of strain in other samples of coated substrates, is suitable for use in this invention. An example of a suitable device is shown in the accompanying drawing. The sample holder 10 is comprised of a base 1, two sample supports 3, and a distortional bar 4. The two sample holders support the sample 2 and are aided by sample restraints 7, which restrict movement of the sample along the surface of the sample supports. The deformational bar slides onto machine screws 8 in a direction perpendicular to the sample surface. A constant level of strain is applied to the coated substrate by tightening nuts 9 so as to force the deformational bar onto the surface of the coated substrate. A constant level of strain is applied to the coated substrate provided the screws remain in a fixed position. The stress applied to the coated substrate varies along its surface with the maximum stress being applied at the point of contact with the deformational bar. Samples within such an apparatus can be tested for delayed failure in a QUV test, Florida test or any test which measures the extent of degradation from heat, moisture and/or ultraviolet light. The level of strain and the degree of stress applied can be reproduced with other samples of coated substrates by merely tightening the nuts to the same position as used previously.

Other devices are also suitable for carrying out this process. For example, modifications of the device shown in the accompanying drawing are suitable. These would include devices with two or more deformational bars or those which deform the sample at a specific point on the coating rather than along the length of the coating. Another device which is suitable is the microcracker decribed by Anthony and LeGrand in copending application, Ser. No. 572,482. Although more sophisticated than the device shown in the accompanying drawing, a coated substrate may be placed under a constant level of tensional strain by the device which is also recorded by the device. This level of tensional strain can be reproduced when evaluating other samples of coated substrates for comparison.

The method comprising the invention will accelerate the delayed failure of most coated substrates. Examples of such coated substrates include substrates coated with the silicone resin coating compositions described in U.S. Pat. Nos. 4,277,287 and 4,278,804, and pending application Ser. No. 373,361 which are incorporated herein by reference. These silicone resin coating compositions are used on a wide variety of surfaces, including plastic surfaces and metal surfaces. Examples of such plastics include synthetic organic polymeric substrates, such as acrylic polymers, polyesters, polyamides, polyimides, acrylonitrile-styrene copolymers, styrene-acrylonitrile-butydieneterpolymers, polyvinylchloride, butyrates, polyethylene polymers, polycarbonate polymers, etc.

A special mention is made of the polycarbonates, such as those polycarbonates known as Lexan ® polycarbonate resin, available from General Electric Company. Other types of substrates on which the silicone resin coating compositions can be utilized include wood, glass, ceramics, etc.

In general, the silicone resin coating compositions which provide the silicon resin coatings are comprised of the hydrolysis product of an aqueous dispersion of colloidal silica and a trifunctional silane of the formula, $RSi(OCH_3)_3$, wherein R is an alkyl radical of from 1 to 3 carbon atoms. These compositions comprise from about 10 to 50 weight percent solids dispersed in a water/alcohol dispersion medium, said solids comprise from 10-70 weight % colloidal silica and 30-90 weight % of the trifunctional silane described above. At least 70% of these silanes are $CH_3Si(OCH_3)_3$. These compositions may also contain additives such as ultraviolet light absorbing agents, antioxidants, thickening agents, pigments, dyes, cure catalysts and flow modifiers.

This process will also provide accelerated delayed failure times for painted substrates comprising coatings selected from acrylic, urethane and latex paints and substrates selected from those given above for silicone resin coatings.

The following examples are provided to illustrate the invention. It is not intended to limit the invention to the embodiments they describe.

EXAMPLE

A silicone resin coating composition utilized to provide the coated substrate in this example was prepared in the following manner. Methyltrimethoxysilane (20.3 grams), acetic acid (0.06 grams) and Ludox LS colloidal silica having 30% colloid (16.7 grams) were added to a reaction vessel and stirred at a temperature within the range of 20°–30° for 16 hours. Isobutanol (38 grams) was introduced, followed by 0.6 grams of a polysiloxane-polyether copolymer flow modifier described in U.S. Pat. No. 3,629,165 and sold by General Electric Company as SF-1066. In addition, 3.2 grams of a silylated hydroxybenzyphenone ultraviolet light absorbing agent described by Anthony in copending applications Ser. Nos. 373,361 and 572,482 was added.

The mixture was stirred at room temperature for 10 days before use. The composition was then applied to a Lexan ® polycarbonate substrate in the following manner. The silicone resin coating composition was flow coated onto a one-foot square Lexan sheet to a thickness of 0.00024" which had been primed. The coating was allowed to air dry for 30 minutes and then cured in a hot-air oven for 90 minutes at 130° C. The sheet was removed from the oven and allowed to cool to room temperature. The sheet was cut into 4 strips 3" wide and 12" long.

The coated substrate samples were then placed into 4 separate devices of the type illustrated in the accompanying drawing. The nuts on the devices were then tightened until the samples had been bent to achieve various levels of strain on the coatings. The level of strain, $\epsilon$, obtained for each sample was determined as $4\Delta Dt/L^2$, wherein L is the distance between the sample supports and $\Delta D$ is the distance the sample is moved (distorted) by the distortional bar from its position at zero strain and t is the thickness of the sample. The values for strain are indicated below in Table I.

The devices were then placed in a QUV testing apparatus sold by Q-Panel Company. The samples were exposed to 8 hours of ultraviolet light at about 70° C. and then allowed to cool for 4 hours in darkness to permit condensation. This cycle was repeated until cracks or flaws were observed. The times for failure of these samples are given in Table I.

TABLE I

| Time of Failure for Strained Samples | |
|---|---|
| Strain $\epsilon \left( \dfrac{in}{in} \right)$ | Time of Failure (hrs) |
| 0 | 1000 |
| .0018 | 400 |
| .0033 | 120, 160 |
| .0041 | 150 |
| .0049 | 30, 40, 50 |
| .0054 | 22 |

Although the Example above is an illustration of the present invention, further modifications are possible in light of the above techniques by one skilled in the art without departing from the scope and spirit of this invention.

What is claimed is:

1. A method for predicting the useful lifetime of a coated substrate which comprises subjecting said substrate to a controlled level of stress while simultaneously exposing it to a Florida test and measuring the time required to detect failure.

2. A method as in claim 1 wherein the coated substrate is comprised of a
   (a) silicon resin coating obtained from a composition comprised of from about 10 to about 50 weight percent solids dispersed in a water/alcohol dispersion medium, said solids comprising from about 10–70 weight percent colloidal silica and about 30–90 weight percent of a partial condensate obtained from a trifunctional silane having the formula, $RSi(OCH_3)_3$, wherein R is selected from the group consisting of alkyl radicals having from 1 to 3 carbon atoms, at least 70% of which is $CH_3Si(OCH_3)_3$, and
   (b) a substrate selected from the group consisting of glass, ceramics, acrylic polymers, polyesters, polyamides, polyimides, acrylonitrile-styrene copolymers, styrene-acrylonitrile-butadieneterpolymers, polyvinyl chloride, butyrates, polyethylene polymers, polycarbonate polymers and mixtures thereof.

3. A method as in claim 2 wherein the composition which provides the silicon resin coating of said coated substrate additionally contains one or more additives selected from the group consisting of ultraviolet light absorbing agents, antioxidants, thickening agents, pigments, dyes, cure catalysts and flow modifiers.

4. A method as in claim 3 wherein the substrate of said coated substrate is comprised of polycarbonate polymers.

5. A method as in claim 1 wherein the level of strain applied to the coated substrate falls within the range of about 0.001 to 0.009 in/in.

6. A method as in claim 1 wherein the atmospheric elements of the Florida test consist of moisture, humidity, heat, and ultraviolet light.

7. An accelerated QUV test for predicting the useful lifetime of a coated substrate which comprises exposing said substrate to a controlled level of stress while simultaneously subjecting it to a QUV test and measuring the time required to detect failure.

* * * * *